(12) United States Patent
Lee et al.

(10) Patent No.: US 10,549,010 B2
(45) Date of Patent: Feb. 4, 2020

(54) LIPID-FREE SCAFFOLDS FOR HUMAN VOLUME REPLACEMENT OR CELL CULTURE AND USE THEREOF

(75) Inventors: Heeyoung Lee, Jeollabuk-do (KR); Hyunjin Yang, Seoul (KR); Jun Seok Lee, Busan (KR); Ji Suk Choi, Seoul (KR)

(73) Assignee: Heeyoung Lee, Seoul (KR)

( * ) Notice: Subject to any disclaimer, the term of this patent is extended or adjusted under 35 U.S.C. 154(b) by 859 days.

(21) Appl. No.: 12/601,518

(22) PCT Filed: Mar. 24, 2008

(86) PCT No.: PCT/KR2008/001632
§ 371 (c)(1),
(2), (4) Date: Nov. 23, 2009

(87) PCT Pub. No.: WO2008/143402
PCT Pub. Date: Nov. 27, 2008

(65) Prior Publication Data
US 2010/0178681 A1     Jul. 15, 2010

(30) Foreign Application Priority Data
May 18, 2007  (KR) .................. 10-2007-0048392

(51) Int. Cl.
*A61L 27/36*     (2006.01)

(52) U.S. Cl.
CPC ............................... *A61L 27/3604* (2013.01)

(58) Field of Classification Search
None
See application file for complete search history.

(56) References Cited

U.S. PATENT DOCUMENTS

| 4,294,251 A | * | 10/1981 | Greenwald et al. | 604/28 |
| 4,707,369 A | * | 11/1987 | Suresky | 426/417 |
| 4,801,299 A | * | 1/1989 | Brendel et al. | 623/1.47 |
| 7,615,373 B2 | * | 11/2009 | Simpson | A61F 2/08 435/398 |
| 7,902,145 B2 | * | 3/2011 | Chu | A61L 2/0011 435/1.3 |

FOREIGN PATENT DOCUMENTS

| EP | 0418979 | * | 3/1991 | C08H 1/06 |
| EP | 0448770 | * | 10/1991 | C07K 15/00 |
| WO | 2005/035739 A1 | | 4/2005 | |
| WO | 2005/055814 A3 | | 6/2005 | |
| WO | 2006/112684 A1 | | 10/2006 | |

OTHER PUBLICATIONS

Novakofski et al., Journal of Animal Science, vol. 65 (Suppl. 2), pp. 12-24, 1987.*
Parrish et al., BBA, Biochemica et Biophysica Acta 1323 (1997) pp. 253-262.*
Oil Red O Product Datasheet, retrieved from the internet, Aug. 24, 2015: www.abcam.com/oil-red-o-lipid-stain-ab150678.html.*
Membranes Organize Cellular Complexity, retrieved from the internet, Aug. 24, 2015: learn.genetics.utah.edu/content/cells/membranes/.*
Encyclopaedia Britannica: Connective tissue, retrieved from the internet Mar. 21, 2016: www.britannica.com/science/connective-tissue.*
Japanese Office Action dated Sep. 11, 2012 Appln. No. 2010-509263.

* cited by examiner

*Primary Examiner* — Renee Claytor
*Assistant Examiner* — Evelyn Y Pyla
(74) *Attorney, Agent, or Firm* — Ladas & Parry LLP

(57) ABSTRACT

The present invention relates to lipid removed scaffolds (lipid-free scaffolds) for human tissue volume replacement or cell culture. More particularly, the present invention relates to a method for preparing lipid removed scaffolds (lipid-free scaffolds) for human tissue volume replacement or cell culture, the method comprising the steps of: fragmenting fat tissue to isolate lipids by ultrasonic treatment or high pressure nozzle spray; removing the isolated lipids and fat tissue from which lipids were not isolated to sterilize. According to the present invention, lipids are removed from fat tissue only by physical treatment to maintain the volume thereof and microstructures such as cellular membrane as much as possible and thus the inventive scaffolds are useful for human tissue volume replacement.

14 Claims, 1 Drawing Sheet

LIPID-FREE SCAFFOLDS FOR HUMAN VOLUME REPLACEMENT OR CELL CULTURE AND USE THEREOF

CROSS-REFERENCES TO RELATED APPLICATIONS

This application is a U.S. national phase application, pursuant to 35 U.S.C. § 371, of PCT/KR2008/001632, filed Mar. 24, 2008, designating the United States, which claims priority to Korean Application No. 10-2007-0048392, filed May 18, 2007. The entire contents of the aforementioned patent applications are incorporated herein by this reference.

TECHNICAL FIELD

The present invention relates to lipid removed scaffolds (lipid-free scaffolds) for human tissue volume replacement or cell culture, and more particularly, to a method for preparing lipid removed scaffolds(lipid-free scaffolds) for human tissue volume replacement or cell culture, the method comprising: fragmenting fat tissue to isolate lipids from the fat tissue fragments by ultrasonic treatment or high pressure nozzle spray method; removing the isolated lipids as well as fat tissue from which lipids were not isolated; and sterilizing the remaining fat tissue fragments.

BACKGROUND ART

A variety of artificial materials for human tissue volume replacement have been developed and practically used in diverse applications, however, these involve a significant problem of gradual volume reduction.

Allogenic dermis or allogenic bone of human or animal origin has been used as a transplant material after processing the same. However, the process thereof is complicated and causes extended time consumption to get permission from authorities since various chemical methods are additionally applied to the processing to eliminate antigenicity of human immune proteins and cells. Also, the processing has other disadvantages in that this cannot completely eliminate antigenicity to cause adverse side effects, requires considerable processing costs, and the supply of cadaver as raw material is limited and thus cadaver is being purchased at the high price of 500,000 won per 1 cc of the cadaver.

A variety of artificial skin equivalents are now being developed, more particularly, many products such as acellular artificial skin, hierarchically layered (a two-layer structure of) cellular living skin equivalents (LSE) prepared by culturing epidermal and dermal cells of a patient oneself, etc. were developed and they are in the pre-commercial phase. Such products are very expensive since they are manufactured by decellularizing allogenic tissue or using biomaterials such as collagen.

Cellular artificial skin derived from human bodies has excellent wound recovery effect in the qualitative aspect of medical treatment, for example, rapid wound healing, scar reduction and so on. This artificial skin is also reported to exhibit no immune rejection response caused by autologous cells or processed allogenic tissues.

Matrix-type artificial skins using chitosan, collagen, chitin, etc. are commercialized and alternative skins, which were newly developed by culturing skin cells on the matrix, are now in clinical trials. However, mass production of these products has not been accomplished.

Korean Patent No. 10-0469661 disclosed a method for preparing an acellular dermal graft to manufacture and provide a product named "SureDerm", thus achieving domestic production of some of biomaterials for tissue regeneration, which have usually been imported from overseas.

However, since there are many restrictions in securing domestic supply of human skins, raw materials are mostly imported to manufacture artificial skin products.

In general, the above artificial skin products referred to as "filler" are usually manufactured using animal-derived materials, synthetic materials and human-derived tissues as raw materials, but they have several disadvantages in terms of convenience of use, durability and price thereof.

Another products include, for example: ZYDERM® for injection manufactured using bovine collagen; ARTECOLL® which is a mixture of polymethyl methacrylate beads suspended in collagen; RESTYLANE® which is a modified hyaluronic acid; CYMETRA® is a powdered form of ALLODERM®, and the like.

ALLODERM® commercially available from LifeCell is a human allogenic acellular dermal matrix prepared by decellularization of cadaver dermis, and is used as a graft or an insert. This product has advantages of; completely eliminating the possibility of immune rejection by removing all of cells from raw material; and exhibiting high biocompatibility compared to any other conventional artificial skin product due to use of natural human tissue. Accordingly similar products have also been developed in domestic fields, but it is difficult to find skin donors, thus resulting in import of raw materials from overseas.

Generally, fat tissue extracted from obese patients is discarded or partially stored for further use. Triacylglycerol in lipid droplets, which is contained in a great amount in tissue, or neutral lipids such as sterol esters may be deteriorated by oxidation or partial oxidation and hydrolysis, so that it is difficult to store fat tissue for over 2 months to reuse.

Lipid oxidation causes discoloration or lipid loss by a reaction between a reactant obtained through oxidation of polyunsaturated fatty acid and amino compounds such as proteins, and generates toxic materials such as hydroperoxide, unsaturated aldehyde, etc. Furthermore, fat tissue from animals excluding humans, for example, pigs or cows, etc, has low liquid lipid content (50 to 70%), and is partially mixed with panniculus muscularis. On the other hand, human fat tissue is clearly distinguished from dermal tissue or muscle layer and has exceedingly high content of liquid lipid and thus there has not yet been any attempt to develop a novel biological graft material by processing human fat tissue.

Meanwhile, an artificial substrate means a support material capable of forming a three-dimensional matrix into which tissue cells taken from a donor were seeded, and are often referred to as carriers or artificial scaffolds. Such scaffolds must satisfy the following conditions:

First, the scaffolds should maintain the morphological structure of biotissues to be regenerated; second, they should efficiently induce adhesion, growth and differentiation of cells to be cultured; third, they should exhibit high biocompatibility; forth, they must be safely absorbed and degraded in vivo after completion of the scaffolding. For the development of technologies for an ultra-precision three dimensional artificial scaffold to regenerate biotissues, manufacturing artificial scaffolds for tissue regeneration to efficiently differentiate into specific tissue cells and producing biocompatible materials substantially similar to the biotissues are two key technologies.

For example, scaffolds for bone and soft tissue regeneration include various synthetic materials such as synthetic or natural calcium phosphate, polylactic acid or polyglycolic acid; collagen; and cellulose based natural polymers, etc. Materials used to manufacture scaffolds for facilitating tissue regeneration must have microstructure and chemical composition suitable for optimal cell growth and cell function. For bone regeneration, these materials must have similar physical, chemical and mechanical properties to the host bone because such properties may influence normal bone growth and bone function. Recently, a lot of studies on natural polymers have been carried out, and particularly, there are many researches on the use of chitosan and biological materials.

However, since there is a limitation in the use of tissue-compatible biomaterials which are decomposed in vivo, and tissue engineering technologies enabling differentiation into various body tissues are still insufficient, there are limitations in reproducibility of the function of each organ in human body.

In addition, although tissue-compatible micropowder is being used as a micropowder for three-dimensional cell culture, biocompatible materials such as poly L-lactic acid (PLLA), poly lactic-co-glycolic acid(PLGA), which are used as a micropowder for cell culture, cost more than 500,000 won per 1 g of material. In particular, for cell culture, a structure similar to that of human tissue should be formed, but high precision molding is not developed sufficiently enough to form a human tissue-like structure.

The biomaterials used in biodegradable micropowders such as polylactic acid(PLA), polyglycolic acid(PGA), etc. to manufacture artificial scaffolds are prepared by conventional processes including, for example: gas foaming/salt leaching; high pressure gas expansion; emulsion freeze-drying; solvent-casting/particulate leaching technique; phase separation, and the like.

However, these processes have drawbacks such as low reproducibility and limitation in manufacturing high precision and complex three-dimensional structures. Additionally, in case of manufacturing porous structures, the above processes have problems in that it is difficult to freely control pore size and porosity, they show low interconnectivity between pores, thus causing difficulties in cell growth, nutrition supply, diffusion and transfer of cells into artificial scaffolds and an extended period of time for production thereof is required.

Fat tissue has difficulties in storage or transplantation since it consists of liquid lipid which amounts to 98% of the total tissue volume, and involves all variables upon cell culture such that there has been no attempt to develop materials for transplantation using fat tissue.

However, fat tissue volume can be partially maintained if lipids are removed from fat tissue while maintaining microstructure thereof. Accordingly, it is assumed that fat tissue can play a significant role as a biomaterial.

Recently, there are some reports disclosing that a sponge-like structure promotes the growth and differentiation of cells. Based on this fact, it is assumed that the volume of material to be transplanted into a human body is more important than the weight of the same in terms of in vivo effects or cell culture.

Consequently, it is expected that fat tissue can be a remarkably beneficial material compared to other biotissues if the fat tissue can maintain microstructures of connective tissue and cell membrane during adipose tissue processing.

Accordingly, the present inventors have made extensive efforts to develop a sponge-like powder with three-dimensional structure, in which the volume of fat tissue is maintained at maximum possible size, lipid oxidation is prevented, and disadvantages of the existing artificial scaffolds are complemented, and as a result, they confirmed that when adipose tissue lipids are physically removed and dried, the fat tissue can be used as scaffolds for human tissue volume replacement by injecting them for transplantation and at the same time, can be used as scaffolds for cell culture, thereby completing the present invention.

SUMMARY OF INVENTION

The main object of the present invention is to provide lipid removed scaffolds(lipid-free scaffolds) for human tissue volume replacement or cell culture, and a method for preparing the same.

In order to accomplish the above objects, the present invention provides scaffolds for human tissue volume replacement or cell culture, which is prepared by removing lipids from fat tissue.

The present invention also provides a method for preparing scaffolds for human tissue volume replacement or cell culture, the method comprising the steps of: (a) fragmenting fat tissue to isolate lipids from the fat tissue fragments by sonification; (b) removing the isolated lipids and fat tissue from which lipids were not isolated; and (c) sterilizing the resulting lipid-free fat tissue to produce scaffolds from which lipids were removed.

In the present invention, the step (a) is preferably carried out by treating the fat tissue fragments with hyaluronidase, and then ultrasound.

The present invention also provides a method for preparing scaffolds for human tissue volume replacement or cell culture, the method comprising the steps of: (a) fragmenting fat tissue to isolate lipids from the fat tissue fragments by high pressure nozzle spray method; (b) removing the isolated lipids and fat tissue from which lipids were not isolated; and (c) sterilizing the resulting lipid-free fat tissue to produce scaffolds from which lipids were removed.

In the present invention, the step (a) is preferably performed without using protease, and the step (c) preferably further includes drying step for powderization. The lipid is preferably lipid droplets.

In the present invention, the step (b) is preferably conducted by filtration or centrifugation, and preferably further includes a washing step with ethanol or distilled water after the centrifugation. The sterilization is preferably performed by using radiation or ethylene oxide (EO) gas.

Other features and embodiments as well as the above objects of the present invention will become more apparent to those skilled in the related art by the following detailed description and appended claims.

DETAILED DESCRIPTION OF THE INVENTION, AND PREFERRED EMBODIMENTS

A preferred embodiment of the present invention is to provide lipid removed scaffolds(lipid-free scaffolds) for human tissue volume replacement or cell culture and a method for preparing the same.

In the present invention, fat tissue discarded after extracted from obese patients was fragmented and subjected to sonication to isolate lipids. The isolated lipids and fat tissue, from which lipids were not isolated, were filtered, centrifuged, and washed with 70% ethanol, then distilled water to remove as much lipids such as triacylglycerol, sterol ester, etc in cells as possible.

Subsequently, the lipid-free fat tissue was lyophilized or air dried and, sterilized using radiation or EO gas to obtain a lipid-free powder.

Figure 2:
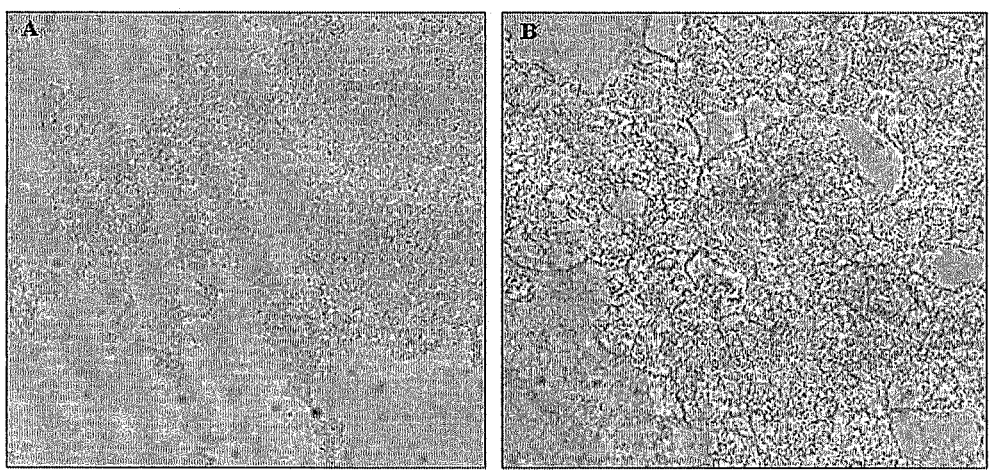
FIG. 2 shows the results of staining lipid-free powder of the present invention with oil red O (A: ×200 magnification, B: ×400 magnification).

In the present invention, since fat tissue is not treated with proteases such as collagenase, lipase, trypsin, etc., to maintain red blood cells, extracellular matrix, etc., the volume and three-dimensional structure of the lipid removed scaffolds(lipid-free scaffolds) can be maintained (see FIG. 2).

The protease treatment can cause safety problems in vivo so that it requires an additional washing process and has a problem in obtaining Korea Food and Drug Administration Approval.

In contrast, the lipid removed scaffolds(lipid-free scaffolds) for human tissue volume replacement and cell culture according the present invention have advantages such as increased productivity and improved quality.

In the sonication, hyaluronidase can be added for separation of cells.

Fat tissue discarded after extracted from obese patients was fragmented and subjected to high pressure nozzle spray to isolate lipids from the fragments. Such isolated lipids and fat tissue, from which lipids were not isolated, were filtered, centrifuged, and washed with 70% ethanol, then distilled water, so as to remove as much lipids such as triacylglycerol, sterol ester and the like in cells as possible. The lipid-free fat tissue fragments were lyophilized or air dried and sterilized using radiation or EO gas, thus obtaining a lipid-free powder.

After the high pressure nozzle spray, protein denaturation can be minimized by washing only with distilled water. Herein, protein denaturation was minimized under the assumption that even autologous tissue can cause immune rejection response due to the protein denaturation.

As a result of staining the lipid-free powder with oil red O, it was demonstrated that the powder did not contain lipids.

In addition, if the lipids remain in the fat tissue, it will not be powderized so that the fat tissue powderization can be used to determine whether lipids are present therein.

In the present invention, "for human tissue volume replacement" as used herein means transplantation of fat tissue for the purpose of: the correction of contour deformities in the skin, such as fine to deep wrinkles and the modification of the contours of the face and body; and regeneration of deformed sites throughout the human body including, for example, defects from cancer surgery, injury sites, etc.

In case where fat tissue is used as a material for human tissue volume replacement, it must comprise biocompatible material to reduce adverse side effects on the human body. Herein, any chemical treatment such as enzyme treatment must be substantially limited.

When lipids are removed from fat tissue, it is possible to store for long period of time and maintain the volume and microstructures such as cell membrane, and thus, fat tissue can be used as a transplant material.

Furthermore, the lipid-free powder prepared in the form of powder according to the present invention has the surface area for cell adhesion and high biocompatibility, thus making it possible to use as scaffolds for cell culture.

EXAMPLES

Hereinafter, the present invention will be described in further detail with reference to examples. It is to be understood, however, that these examples are for illustrative purposes only and are not to be construed to limit the scope of the present invention.

Although the following examples used fat tissue extracted from obese patients, fat tissue extracted from cadaver can be also used for the present invention.

In the following examples, the scaffolds were prepared in the form of powder by drying and sterilizing the fat tissue from which lipid is removed. However, it is clearly understood to those skilled in related art that the fat tissue, from which lipid is removed, can be also used in liquid state without the drying process for preparing the scaffolds.

Example 1: Preparation of Lipid-Free Powder 1-1 (Preparation Example 1)

Fat tissue discarded after extracted from an obese patient was fragmented and subjected to sonication(110 W) 10 to 15 times at 60~80° C. for 10 minutes in distilled water to isolate lipids.

The isolated lipids and fat tissue, from which lipids were not isolated, were filtered or centrifuged at 3500 rpm for 5 minutes, followed by washing with 70% ethanol and distilled water, respectively.

The lipid-free fat tissue fragments were lyophilized or air dried and sterilized using radiation, thereby obtaining a lipid-free powder.

1-2 (Preparation Example 2)

Fat tissue discarded after extracted from an obese patient was fragmented and lipids were isolated from the fat tissue fragments by adding distilled water to the fragments to spray using high pressure nozzle.

The isolated lipids and fat tissue, from which lipids were not isolated, were filtered or centrifuged at 3500 rpm for 5 minutes, followed by washing with 70% ethanol and distilled water, respectively.

The lipid-free fat tissue fragments were lyophilized or air dried and sterilized using radiation, thereby obtaining a lipid-free powder.

1-3 (Preparation Example 3)

Fat tissue discarded after extracted from an obese patient was fragmented and added with distilled water and hyaluronidase at a ratio of 1.1:0.1, followed by sonification (100 W) 10 to 15 times at 60~80° C. for 10 minutes to isolate lipids.

The isolated lipids and fat tissue, from which lipids were not isolated, were filtered or centrifuged at 3500 rpm for 5 minutes, followed by washing with 70% ethanol, then distilled water.

The lipid-free fat tissue fragments were lyophilized or air dried and sterilized using radiation, thereby obtaining a lipid-free powder.

1-4 (Preparation Example 4)

Fat tissue discarded after extracted from an obese patient was fragmented and lipids were isolated from the fat tissue fragments by adding distilled water to the fragments to spray using high pressure nozzle.

The isolated lipids and fat tissue, from which lipids were not isolated, were filtered or centrifuged at 3500 rpm for 5 minutes, followed by washing with distilled water.

The lipid-free fat tissue fragments were lyophilized or air dried and sterilized using radiation or EO gas, thereby obtaining a lipid-free powder.

Example 2: Staining of Lipid-Free Powder

The lipid-free powder prepared in Example 1-1 was stained using oil red O and fat tissue before the powderization process of Example 1-1 was used as a control group.

Figure 1:
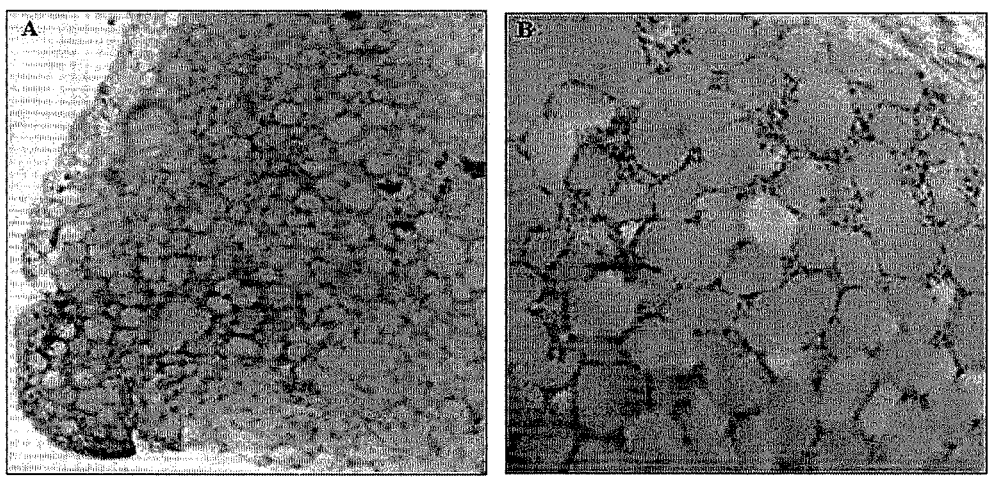
FIG. 1 shows the results of staining fat tissue with oil red O (A: ×40 magnification, B: ×100 magnification).

As a result, it was observed that the control group contained lipids(see FIG. 1) while lipids were completely removed from the lipid-free powder prepared in Example 1-1 (see FIG. 2).

As illustrated from this experiment results, it is understood that the lipid-free fat tissue of the present invention can be used as scaffolds for human tissue volume replacement.

Moreover, the lipid-free fat tissue according to the present invention is in the form of micropowder so that it can be used as scaffolds for cell culture, as shown in FIG. 2.

INDUSTRIAL APPLICABILITY

As described in detail above, the present invention has an effect to provide lipid removed scaffolds(lipid-free scaffolds) for human tissue volume replacement or cell culture and a method for preparing of the same. The inventive lipid removed scaffolds(lipid-free scaffolds) for human tissue volume replacement or cell culture have advantages in that the process thereof is simple since lipids can be removed from fat tissue without chemical treatment such as enzyme treatment, storage period can be increased due to lipid removal and drying process, microstructures such as cellular membrane and the volume thereof can be maintained as much as possible, production cost can be reduced due to recycling of discarded fat tissue, and they are injectable for transplantation due to preparation in powder form.

While the present invention has been described with reference to the above preferred embodiments, it will be understood by those skilled in the art that various modifications and variations may be made therein without departing from the scope of the present invention as defined by the appended claims.

What is claimed is:

1. A method for preparing a scaffold for transplantation of fat tissue for the correction of contour deformities in the skin and/or regeneration of deformed sites throughout the human body or cell culture, the method comprising the steps of;
   (a) fragmenting fat tissue by physical treatments without using any chemical treatment to obtain isolated lipids hi a liquid state, a first fragmented fat tissue containing lipids in a liquid state, and a second fragmented fat tissue free of lipids in a liquid state;
   (b) removing the isolated lipids in a liquid state;
   (c) removing only the first fragmented fat tissue containing lipids in a liquid state to isolate the second fragmented fat tissue free of lipids in a liquid state; and
   (d) sterilizing the second fragmented fat tissue to obtain a scaffold,
   wherein a volume and a three-dimensional structure of the scaffold are partially maintained, and
   wherein a microstructure of the scaffold comprising connective tissue is partially maintained.

2. A method for preparing a scaffold for transplantation of fat tissue for the correction of contour deformities in the skin and/or regeneration of deformed sites throughout the human body or cell culture, the method comprising the steps of:
   (a) fragmenting fat tissue by sonication or high pressure nozzle spray without using any chemical treatment to obtain isolated lipids in a liquid state, a first fragmented fat tissue containing lipids in a liquid state, and a second fragmented fat tissue free of lipids in a liquid state;
   (b) removing the isolated lipids in a liquid state;
   (c) removing only the first fragmented fat tissue containing lipids in a liquid state to isolate the second fragmented fat tissue free of lipids in a liquid state; and
   (d) sterilizing the second fragmented fat tissue to obtain a scaffold,
   wherein a volume and a three-dimensional structure of the scaffold are partially maintained, and
   wherein a microstructure of the scaffold comprising connective tissue is partially maintained.

3. The method according to claim 1 or claim 2, wherein the step (a) is carried out without using protease.

4. The method according to claim 1 or claim 2, which further comprises the step (d) of drying and powderizing the obtained scaffold.

5. The method according to claim 1 or claim 2, wherein the step (b) is conducted by filtration or centrifugation.

6. The method according to claim 5, which further comprises the step of washing the resulting fat tissue with water after the centrifugation.

7. The method according to claim 1 or claim 2, wherein the sterilization is performed using radiation or ethylene oxide (EO) gas.

8. A method for preparing a scaffold for transplantation of fat tissue for the correction of contour deformities in the skin and/or regeneration of deformed sites throughout the human body or cell culture, the method comprising the steps of:
   (a) fragmenting fat tissue by physical treatments without using any chemical treatment to obtain isolated lipid droplets in a liquid state, a first fragmented fat tissue containing lipid droplets in a liquid state, and a second fragmented fat tissue free of lipid droplets in a liquid state;
   (b) removing the isolated lipid droplets in a liquid state;
   (c) removing only the first fragmented fat tissue containing lipid droplets in a liquid state to isolate the second fragmented fat tissue free of lipid droplets in a liquid state; and
   (d) sterilizing the second fragmented fat tissue to obtain a scaffold,
   wherein a volume and a three-dimensional structure of the scaffold are partially maintained, and
   wherein a microstructure of the scaffold comprising connective tissue is partially maintained.

9. A method for preparing a scaffold for transplantation of fat tissue for the correction of contour deformities in the skin and/or regeneration of deformed sites throughout the human body or cell culture, the method comprising the steps of:
   (a) fragmenting fat tissue by sonication or high pressure nozzle spray without using any chemical treatment to obtain isolated lipid droplets in a liquid state, a first fragmented fat tissue containing lipid droplets in a liquid state, and a second fragmented fat tissue free of lipid droplets in a liquid state;
   (b) removing the isolated lipid droplets in a liquid state;

(c) removing only the first fragmented fat tissue containing lipid droplets in a liquid state to isolate the second fragmented fat tissue free of lipid droplets in a liquid state; and (d) sterilizing the second fragmented fat tissue to obtain a scaffold, wherein a volume and a three-dimensional structure of the scaffold are partially maintained, and wherein a microstructure of the scaffold comprising connective tissue is partially maintained.

10. The method according to claim 8 or 9, wherein the step (a) is carried out without using protease.

11. The method according to claim 8 or 9, which further comprises the step (d) of drying and powderizing the obtained scaffold.

12. The method according to claim 8 or 9, wherein the step (b) is conducted by filtration or centrifugation.

13. The method according to claim 12, which further comprises the step of washing the resulting fat tissue with water after the centrifugation.

14. The method according to claim 8 or 9, wherein the sterilization is performed using radiation or ethylene oxide (EO) gas.

* * * * *